US 011141183B2

(12) United States Patent
Li et al.

(10) Patent No.: US 11,141,183 B2
(45) Date of Patent: Oct. 12, 2021

(54) WAVEGUIDE ROD FOR ULTRASONIC SCALPEL

(71) Applicants: SHANGHAI YISI MEDICAL TECHNOLOGY CO., LTD., Shanghai (CN); YISI (SUZHOU) MEDICAL TECHNOLOGY CO., LTD., Jiangsu (CN)

(72) Inventors: Zhidong Li, Shanghai (CN); Ruixuan Liu, Shanghai (CN); Yu Zhang, Shanghai (CN); Honglin Nie, Shanghai (CN); Xiufeng Shi, Shanghai (CN)

(73) Assignees: YISI (SUZHOU) MEDICAL TECHNOLOGY CO., LTD., Jiangsu (CN); EZISURG MEDICAL CO., LTD., Shanghai (CN)

( * ) Notice: Subject to any disclaimer, the term of this patent is extended or adjusted under 35 U.S.C. 154(b) by 224 days.

(21) Appl. No.: 16/316,798

(22) PCT Filed: Jun. 27, 2017

(86) PCT No.: PCT/CN2017/090329
§ 371 (c)(1),
(2) Date: Jan. 10, 2019

(87) PCT Pub. No.: WO2018/010541
PCT Pub. Date: Jan. 18, 2018

(65) Prior Publication Data
US 2019/0314051 A1      Oct. 17, 2019

(30) Foreign Application Priority Data
Jul. 11, 2016  (CN) .......................... 201610542545.4

(51) Int. Cl.
*A61B 17/32* (2006.01)
*A61B 17/3211* (2006.01)

(52) U.S. Cl.
CPC .. *A61B 17/320068* (2013.01); *A61B 17/3211* (2013.01); *A61B 2017/320082* (2017.08); *A61B 2017/320089* (2017.08)

(58) Field of Classification Search
CPC ........ A61B 17/320068; A61B 17/3211; A61B 2017/320082; A61B 2017/320089
(Continued)

(56) References Cited

U.S. PATENT DOCUMENTS 9,282,990 B2  3/2016 Yamada et al.
2002/0124617 A1  6/2002 Robert et al.
(Continued)

FOREIGN PATENT DOCUMENTS

CN     1889890 A    11/2004
CN     1684635 A    10/2005
(Continued)

OTHER PUBLICATIONS

Office Action dated Dec. 24, 2019 in Russian Application 2019103593.
International Search Report and Written Opinion dated Oct. 11, 2017 in International Application PCT/CN2017/090329.
Office Action dated Mar. 14, 2021 in India Application 201947001436.

*Primary Examiner* — Hafizur Rahman
(74) *Attorney, Agent, or Firm* — Pillsbury Winthrop Shaw Pittman LLP

(57) ABSTRACT

A waveguide rod for an ultrasonic scalpel having a relatively desirable amplitude and frequency comprises a proximal gain structure, a distal gain structure, an intermediate structure, and a frequency adjustment structure. The proximal gain structure and the intermediate structure are connected in a position near an antinode of longitudinal vibration of the waveguide rod through a proximal side gain step. The distal gain structure and the intermediate structure are connected in a position near an antinode of the longitudinal vibration of the waveguide rod through a distal side gain step. The intermediate structure comprises N (N>0, and N is an (Continued)

integer) gain holding structures that are connected two by two in a position near an antinode of the longitudinal vibration of the waveguide rod through an intermediate gain step. X (X>0, and X is an integer) frequency adjustment structures exist on the gain holding structure. The waveguide rod provides an ultrasonic scalpel with a relatively large blade amplitude and also enables the ultrasonic scalpel to work at a stable and suitable vibration frequency, so that the ultrasonic scalpel can cut human tissue efficiently.

28 Claims, 3 Drawing Sheets

(58) Field of Classification Search
USPC .......................................................... 606/169
See application file for complete search history.

(56) References Cited

U.S. PATENT DOCUMENTS

| | | |
|---|---|---|
| 2004/0127926 A1 | 7/2004 | Beaupre |
| 2005/0096679 A1 | 5/2005 | Stulen et al. |
| 2007/0282332 A1 | 12/2007 | Witt et al. |
| 2013/0338691 A1 | 12/2013 | Young et al. |

FOREIGN PATENT DOCUMENTS

| | | |
|---|---|---|
| CN | 101495050 A | 7/2009 |
| CN | 104027156 A | 9/2014 |
| CN | 105962996 A | 9/2016 |
| CN | 206285143 U | 6/2017 |
| SU | 1438745 A1 | 11/1988 |
| SU | 1507352 A1 | 9/1989 |
| WO | 9816157 A1 | 4/1998 |

WAVEGUIDE ROD FOR ULTRASONIC SCALPEL

CROSS REFERENCE TO RELATED APPLICATION

This application is a national stage application, filed under 35 U.S.C. § 371, of International Application No. PCT/CN2017/090329, filed on Jun. 26, 2017, entitled "ULTRASONIC SCALPEL WAVEGUIDE SHAFT," which claims priority to Chinese Patent Application No. 201610542545.4 filed on Jul. 11, 2016, which is incorporated herein by reference in its entirety.

TECHNICAL FIELD

This application relates to ultrasonic surgical instruments, and specifically, to an ultrasonic scalpel having a waveguide rod.

BACKGROUND ART

In current clinical fields, due to advantages such as neat incisions, rapid hemostasis, small thermally damaged regions, and little smoke, ultrasonic scalpels have been used increasingly widely in place of conventional minimally invasive surgical instruments such as high-frequency electric scalpels and mechanical clamps. The ultrasonic scalpel uses an ultrasonic frequency generator to generate mechanical vibration in a blade at a particular ultrasonic frequency to vaporize water molecules in tissue, break hydrogen bonds in proteins, and wreck cells, so as to achieve the objective of tissue cutting, blood coagulation, and vascular closure. Related researches proved (see "Working Principles and Clinical Applications of Ultrasonic Scalpels", LIN Guoqing, QU Zhe, Chinese Medical Equipment Journal, 2008, and "Optimized Design of Ultrasonic Scalpels", ZHOU Hongsheng, XU Xiaofang, et al., Technical Acoustics, February, 2012) that when a mechanical vibration whose particle acceleration is $5 \times 10^4$ g (g is the gravitational acceleration) is applied on living biological tissue, the position where the mechanical vibration is applied can be cut open rapidly without damaging surrounding tissue. A relationship among the amplitude, frequency, and acceleration of a blade of an ultrasonic scalpel is: $a = A(2\pi f)^2$, wherein a is an acceleration, A is an amplitude, and f is a vibration frequency. Therefore, the vibration frequency and amplitude of the blade of the ultrasonic scalpel represent a cutting capability of the blade of the ultrasonic scalpel.

An ultrasonic scalpel generally comprises a main unit, a transducer, a waveguide rod, a blade, an auxiliary mechanism connecting and supporting the foregoing parts, and other accessories. The main unit generates a high-frequency current. The transducer converts the high-frequency current into an ultrasound vibration. Ultrasonic energy is then transferred to the blade through the waveguide rod. The blade contacts human tissue and friction is generated between the blade and the human tissue to produce effects of mechanical cutting and blood coagulation. Generally, the transducer and the waveguide rod are threaded together, and the waveguide rod and the blade may be threaded, welded or directly integrated. During normal working, the transducer, the waveguide rod, and the blade resonate at a resonance frequency. During transfer of the ultrasound vibration from the transducer to the blade through the waveguide rod, in one aspect, the vibration needs to be amplified to provide the blade with a sufficient amplitude, and in another aspect, the waveguide rod is a critical factor for keeping a vibration frequency of the blade stable and suitable. Therefore, the design of the waveguide rod needs to consider both a vibration frequency and an amplitude gain. Persons skilled in the art are always seeking for a waveguide rod structure that has both a stable and suitable vibration frequency and a relatively large amplitude gain.

Patent CN200480036431.8 discloses an ultrasonic scalpel having a gain step, wherein a distance between a gain step and a vibration node on a waveguide rod is set to obtain a relatively large blade amplitude. Patent CN201410068159.7 discloses an ultrasonic scalpel having a waveguide rod with a periodically repetitive structure. The repetitive structure can enable the ultrasonic scalpel to work at a stable frequency. However, the structures disclosed in the foregoing patent deal with only one of an amplitude and a frequency of a waveguide rod rather than take both an amplitude and a frequency into consideration.

SUMMARY OF THIS APPLICATION

In view of the foregoing deficiencies in the prior art, this application provides a novel waveguide rod structure for an ultrasonic scalpel, so that an ultrasonic scalpel can have a relatively large blade amplitude and also can work at a stable and suitable vibration frequency. Therefore, the ultrasonic scalpel can cut human tissue efficiently.

To resolve the foregoing technical problem, the Invention adopts the following technical solution:

A waveguide rod for an ultrasonic scalpel comprises a proximal gain structure, a distal gain structure, an intermediate structure, and a frequency adjustment structure on the intermediate structure.

The proximal gain structure and the intermediate structure are connected in a position near an antinode of longitudinal vibration of the waveguide rod through a proximal side gain step.

A gain of the proximal side gain step is greater than or less than a unit gain, and a distance between the proximal side gain step and the antinode is less than 5% of a half wavelength of the longitudinal vibration of the waveguide rod. Preferably, the proximal side gain step is located in a position of the antinode.

The distal gain structure and the intermediate structure are connected in a position near an antinode of the longitudinal vibration of the waveguide rod through a distal side gain step. A gain of the distal side gain step is greater than or less than a unit gain, and a distance between the distal side gain step and the antinode is less than 5% of a half wavelength of the longitudinal vibration of the waveguide rod. Preferably, the distal side gain step is located in a position of the antinode.

One or more proximal gain steps exist on the proximal gain structure, a gain of the proximal gain step is greater than a unit gain, the proximal gain step is in a position near a node of the longitudinal vibration of the waveguide rod, only zero or one most proximal gain step exists in a position near each node, and a distance between the proximal gain step and the node is less than 5% of a half wavelength of the longitudinal vibration of the waveguide rod. Preferably, the proximal gain step is located in a position of a node.

One or more distal gain steps exist on the distal gain structure, a gain of the distal gain step is greater than a unit gain, the distal gain step is in a position near a node of the longitudinal vibration of the waveguide rod, only zero or one most distal gain step exists in a position near each node, and a distance between the distal gain step and the node is less than 5% of a half wavelength of the longitudinal vibration of the waveguide rod. Preferably, the distal gain step is located in a position of a node.

The intermediate structure comprises N (N>0, and N is an integer) gain holding structures that are connected two by two in a position near an antinode of the longitudinal vibration of the waveguide rod through an intermediate gain step, and a distance between each intermediate gain step and the antinode is less than 5% of a half wavelength of the longitudinal vibration of the waveguide rod. Preferably, the intermediate gain step is located in a position of the antinode.

The frequency adjustment structure is disposed on the gain holding structure of the intermediate structure. A quantity of frequency adjustment structures is X (X>0, and X is an integer), and each frequency adjustment structure forms a front frequency modulation gain step and a rear frequency modulation gain step on a gain holding structure.

Only one node of the longitudinal vibration of the waveguide rod exists between the front frequency modulation gain step and the rear frequency modulation gain step, a distance between the front frequency modulation gain step and the rear frequency modulation gain step is less than a distance between two antinodes of the longitudinal vibration that are adjacent to a node, and one of gains of the front frequency modulation gain step and the rear frequency modulation gain step is greater than a unit gain and the other of the gains is less than the unit gain.

According to this application, preferred implementation solutions of the proximal gain structure and the distal gain structure are: 1) The proximal gain structure is located in a range of a first half wavelength of the longitudinal vibration of the waveguide rod, and the proximal gain step is in a position near a first node of the longitudinal vibration of the waveguide rod. 2) The proximal gain structure is located in a range of first two half wavelengths of the longitudinal vibration of the waveguide rod, and the proximal gain step is in a position near a first or second node of the longitudinal vibration of the waveguide rod. 3) The distal gain structure is located in a range of a last half wavelength of the longitudinal vibration of the waveguide rod, and the distal gain step is in a position near a last node of the longitudinal vibration of the waveguide rod. 4) The distal gain structure is located in a range of last two half wavelengths of the longitudinal vibration of the waveguide rod, and the distal gain step is in a position near a last or a second last node of the longitudinal vibration of the waveguide rod. In addition, another implementation solution of the proximal gain structure and the distal gain structure that meets a requirement of this application is also protected by the Invention.

Further, a plurality of preferred implementation forms is used to implement that the intermediate structure comprises N (N>0, and N is an integer) gain holding structures that are connected two by two in a position near an antinode of the longitudinal vibration of the waveguide rod through an intermediate gain step. 1) A quantity N of the gain holding structures on the intermediate structure is equal to 1. 2) A quantity N of the gain holding structures on the intermediate structure is greater than 1, N is an odd number, and a gain sequence of the intermediate gain steps connecting the gain holding structures is: a gain of each of a first intermediate gain step to an ((N−1)/2)th intermediate gain step is greater than a unit gain, and a gain of each of an ((N−1)/2+1)th intermediate gain step to an (N−1)th intermediate gain step is less than the unit gain. 3) A quantity N of the gain holding structures on the intermediate structure is greater than 1, N is an odd number, and a gain sequence of the intermediate gain steps connecting the gain holding structures is: a gain of each of a first intermediate gain step to an ((N−1)/2)th intermediate gain step is less than a unit gain, and a gain of each of an ((N−1)/2+1)th intermediate gain step to an (N−1)th intermediate gain step is greater than the unit gain. 4) A quantity N of the gain holding structures on the intermediate structure is greater than 1, N is an odd number, and a gain sequence of the intermediate gain steps connecting the gain holding structures is formed by sequentially and alternately arranging a gain greater than a unit gain and a gain less than the unit gain. 5) A quantity N of the gain holding structures on the intermediate structure is greater than 1, N is an odd number, and a gain sequence of the intermediate gain steps connecting the gain holding structures is formed by sequentially and alternately arranging a gain less than a unit gain and a gain greater than the unit gain. 6) The quantity N of the gain holding structures is equal to 2, and a gain of an intermediate gain step connecting two gain holding structures is greater than a unit gain. 7) The quantity N of the gain holding structures is equal to 2, and a gain of an intermediate gain step connecting two gain holding structures is less than a unit gain. 8) The quantity N of the gain holding structures is greater than 2, N is an even number, and a gain sequence of the intermediate gain steps connecting the gain holding structures is formed by sequentially and alternately arranging a gain greater than a unit gain and a gain less than the unit gain. 9) The quantity N of the gain holding structures is greater than 2, N is an even number, and a gain sequence of the intermediate gain steps connecting the gain holding structures is formed by sequentially and alternately arranging a gain less than a unit gain and a gain greater than the unit gain. In addition, another implementation solution of the intermediate structure that meets a requirement of this application is also protected by the Invention.

Further, one or more frequency adjustment structures exist on some gain holding structures, and the frequency adjustment structure has two implementation forms: 1) For the front frequency modulation gain step and the rear frequency modulation gain step of the frequency adjustment structure, the gain of the front frequency modulation gain step is less than the unit gain, and the gain of the rear frequency modulation gain step is greater than the unit gain. 2) For the front frequency modulation gain step and the rear frequency modulation gain step of the frequency adjustment structure, the gain of the front frequency modulation gain step is greater than the unit gain, and the gain of the rear frequency modulation gain step is less than the unit gain.

In specific implementation manners of the waveguide rod for an ultrasonic scalpel, the Invention comprises different implementation manners of the foregoing proximal gain structure, distal gain structure, intermediate structure, and frequency adjustment structure.

The foregoing gain steps have a form selected from a stair form, a conical form, an exponential form or a catenary form.

Several benefits can be obtained from one or more implementation forms of the Invention. The waveguide rod for an ultrasonic scalpel of the Invention comprises a proximal gain structure, a distal gain structure, an intermediate structure, and a frequency adjustment structure. The proximal gain structure has a proximal gain step whose gain is greater than a unit gain in a position near a node of longitudinal vibration of the waveguide rod. It is known to persons skilled in the art that a gain step in a position near a node can affect an amplitude gain significantly, wherein a gain step whose gain is greater than the unit gain can effectively amplify an amplitude, and a gain step whose gain is less than the unit gain can effectively attenuate an amplitude. Therefore, the proximal gain structure can provide the waveguide rod with a relatively large initial amplitude gain. Gain holding structures on the intermediate structure are connected two by two in a position near an antinode of the longitudinal vibration of the waveguide rod through an intermediate gain step. It is known to persons skilled in the art that a gain step in a position near an antinode affects an amplitude gain relatively slightly. Therefore, the intermediate structure can ensure that an amplitude of ultrasound is basically not attenuated or amplified during propagation of the ultrasound in the intermediate structure of the waveguide rod. Without attenuation, the effectiveness of amplitude amplification of the proximal gain structure can be kept. Without amplification, a loss during energy transfer can be reduced. Similar to the proximal gain structure, the distal gain structure has a distal gain step whose gain is greater than the unit gain in a position near a node of the longitudinal vibration of the waveguide rod, so that the waveguide rod can be provided with a relatively large secondary amplitude gain. In this way, the waveguide rod uses the proximal gain structure to provide a relatively large initial amplitude gain, uses the intermediate structure to basically keep the amplitude gain from attenuation and amplification, and then uses the distal gain structure to provide a relatively large secondary amplitude gain, so as to eventually provide a relatively large amplitude for the vibration of a blade. The frequency adjustment structure exists on some gain holding structures of the intermediate structure. The frequency adjustment structure is disposed in a position near a node of the longitudinal vibration of the waveguide rod, and two frequency modulation gain steps are formed before and after the node, wherein a gain of one frequency modulation gain step is greater than the unit gain, and a gain of the other frequency modulation gain step is less than the unit gain. Such a structural form only affects an amplitude gain relatively slightly but can effectively adjust a vibration frequency of the waveguide rod, so that the vibration frequency of the waveguide rod is stabilized in a suitable range. In this way, the waveguide rod that comprises the proximal gain structure, the distal gain structure, the intermediate structure, and the frequency adjustment structure can provide an ultrasonic scalpel with a relatively large amplitude during working and also can enable the ultrasonic scalpel to work stably at a suitable working frequency, so that human tissue can be cut efficiently.

DETAILED DESCRIPTION OF EMBODIMENTS

Figure 1:
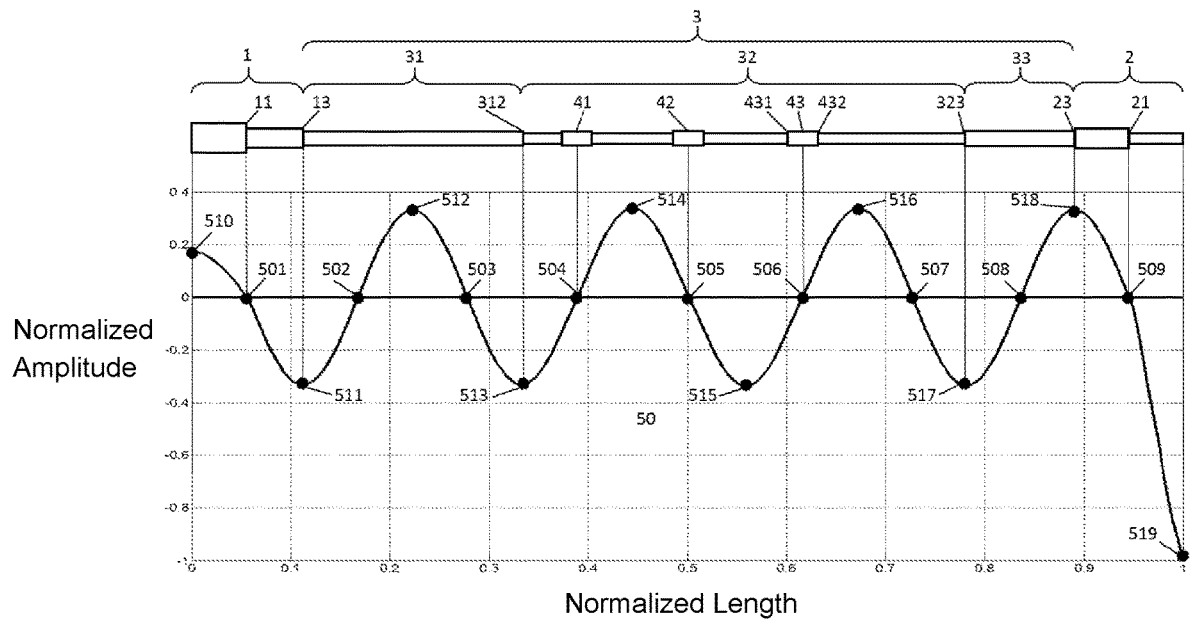
FIG. 1 shows a waveguide rod for an ultrasonic scalpel according to a first implementation manner of this application and a waveform generated along the waveguide rod.

Referring to FIG. 1, FIG. 1 shows a waveguide rod for an ultrasonic scalpel according to a first implementation manner of this application and a waveform generated along the waveguide rod. The waveguide rod for an ultrasonic scalpel comprises a proximal gain structure 1, a distal gain structure 2, an intermediate structure 3, and frequency adjustment structures 41, 42, and 43. A curve 50 below the waveguide rod in FIG. 1 is an amplitude curve of longitudinal vibration of the waveguide rod, wherein a horizontal axis is a normalized length, and a vertical axis is a normalized amplitude. In the curve 50, 501 to 509 are nodes of the longitudinal vibration. The node 501 is a first node, the node 509 is a last node, and 510 to 519 are antinodes of the longitudinal vibration. The antinode 510 is a first antinode, and the antinode 519 is a last antinode. The proximal gain structure 1 and the intermediate structure 3 are connected through a proximal side gain step 13. A position of the proximal side gain step 13 is near the second antinode 511 of the longitudinal vibration, and a gain of the proximal side gain step 13 is greater than a unit gain. The distal gain structure 2 and the intermediate structure 3 are connected through a distal side gain step 23. A position of the distal side gain step 23 is near the second last antinode 518 of the longitudinal vibration, and a gain of the distal side gain step 23 is less than the unit gain.

The proximal gain structure 1 has a most proximal gain step 11 in a position near the first node 501 of the longitudinal vibration of the waveguide rod. A gain of the most proximal gain step 11 is greater than the unit gain. That is, the most proximal gain step 11 is an amplification step. The distal gain structure 2 has a most distal gain step 21 in a position near the last node 509 of the longitudinal vibration of the waveguide rod. A gain of the most distal gain step 21 is greater than the unit gain. That is, the most distal gain step 21 is an amplification step. The proximal gain structure 1 and the distal gain structure 2 set gain steps (that is, the most proximal gain step 11 and the most distal gain step 21) thereof in positions near a node, so that an amplitude gain can be effectively improved. An eventual amplitude gain of the entire waveguide rod is also mainly determined by the gains of the proximal gain structure 1 and the distal gain structure 2. As shown in FIG. 1, the most proximal gain step 11 enables an amplitude gain between the second antinode 511 and the first antinode 510 to be approximately 1.9, and the most distal gain step 21 enables an amplitude gain between the last antinode 519 and the second last antinode 518 to be approximately 3, so that the eventual amplitude gain of the waveguide rod can be up to 5.7. In this way, a relatively large amplitude can be generated in a blade of an ultrasonic scalpel.

The intermediate structure of the waveguide rod 3 comprises N (N>0, and N is an integer) gain holding structures, and comprises three gain holding structures 31, 32, and 33 in the implementation manner in FIG. 1. The first gain holding structure 31 and the second gain holding structure 32 are connected through an intermediate gain step 312. A position of the intermediate gain step 312 is near the fourth antinode 513 of the longitudinal vibration, and a gain of the intermediate gain step 312 is greater than the unit gain. The second gain holding structure 32 and the third gain holding structure 33 are connected through an intermediate gain step 323. A position of the intermediate gain step 323 is near the third last antinode 517 of the longitudinal vibration, and a gain of the intermediate gain step 323 is less than the unit gain. The applicant finds that the structure that the gain holding structures 31, 32, and 33 are connected two by two through a gain step in a position near an antinode of the longitudinal vibration can ensure that an amplitude of an ultrasound vibration is basically not attenuated or amplified during propagation of the ultrasound vibration in the intermediate structure of the waveguide rod, so as to facilitate more stable transfer of energy to the blade.

In some gain holding structures of the intermediate structure 3, in the implementation manner shown in the intermediate structure 3, the frequency adjustment structures 41, 42, and 43 are further disposed on the second gain holding structure 32. Each frequency adjustment structure has a front frequency modulation gain step and a rear frequency modulation gain step. Referring to FIG. 1, the frequency adjustment structure 43 is used as an example. The frequency adjustment structure 43 forms a front frequency modulation gain step 431 and a rear frequency modulation gain step 432 on the gain holding structure 32. A gain of the front frequency modulation gain step 431 is less than the unit gain, and a gain of the rear frequency modulation gain step 432 is greater than the unit gain. Only one node 506 of the longitudinal vibration of the waveguide rod exists between the front frequency modulation gain step 431 and the rear frequency modulation gain step 432. A distance between the front frequency modulation gain step and the rear frequency modulation gain step is less than a distance between the two antinodes 515 and 516 of the longitudinal vibration adjacent to the node 506. The applicant finds that the vibration frequency of the waveguide rod can be adjusted by increasing or reducing a quantity of the frequency adjustment structures, increasing or reducing a distance between a front gain step and a rear gain step of the frequency adjustment structure or increasing or reducing gains of the front gain step and the rear gain step basically without affecting an amplitude eventually output by the waveguide rod. The foregoing frequency adjustment structures 41, 42, and 43 keep a resonance frequency of the waveguide rod in a required range, so that the ultrasonic scalpel can work stably at a suitable frequency.

According to the structural form in FIG. 1 of this application, the proximal gain structure 1 and the distal gain structure 2 provide a relatively large amplitude gain, so as to provide a relatively large amplitude for a vibration of the blade of the ultrasonic scalpel. The gain holding structures 31, 32, and 33 on the intermediate structure 3 can ensure that an amplitude of an ultrasound vibration is basically not attenuated or amplified during propagation of the ultrasound vibration in the intermediate structure of the waveguide rod. The frequency adjustment structures 41, 42, and 43 stabilize the vibration frequency of the waveguide rod in a suitable range. In this way, the ultrasonic scalpel can be provided with a relatively large amplitude during working and also can work stably at a suitable frequency, so that human tissue can be cut efficiently.

Figure 2:
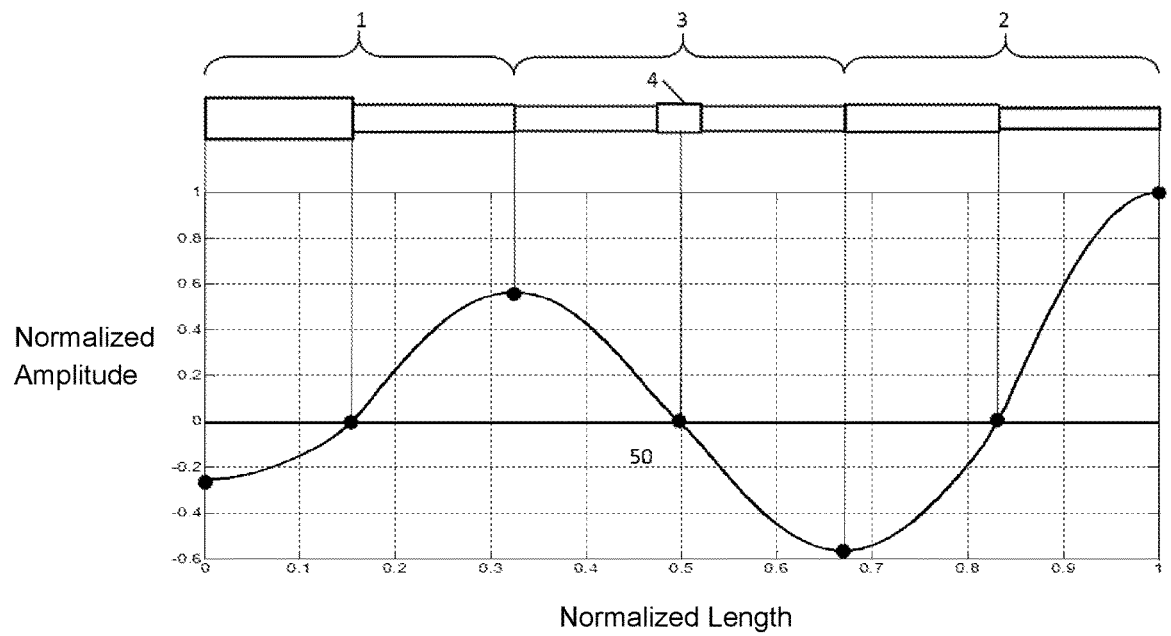
FIG. 2 shows a waveguide rod for an ultrasonic scalpel according to a second implementation manner of this application and a waveform generated along the waveguide rod.

FIG. 2 shows a waveguide rod for an ultrasonic scalpel according to a second implementation manner of this application and a waveform generated along the waveguide rod. The implementation manner comprises a proximal gain structure 1, a distal gain structure 2, an intermediate structure 3, and a frequency adjustment structure 4. The proximal gain structure is in a range of a first half wavelength of longitudinal vibration of the waveguide rod, and a most proximal gain step is near a first node of the longitudinal vibration. The distal gain structure is in a range of a last half wavelength of the longitudinal vibration of the waveguide rod, and a most distal gain step is near a last node of the longitudinal vibration. The proximal gain structure and the intermediate structure are connected in a position near a second antinode of the longitudinal vibration of the waveguide rod, and a gain of a proximal side gain step is greater than a unit gain. The distal gain structure and the intermediate structure are connected in a position near a second last antinode of the longitudinal vibration of the waveguide rod, and a gain of a distal side gain step is less than the unit gain. The intermediate structure in the implementation manner comprises only one gain holding structure. One frequency adjustment structure exists on the gain holding structure. A gain of a front frequency modulation gain step of the frequency adjustment structure is less than the unit gain, and a gain of a rear frequency modulation gain step is greater than the unit gain.

Figure 3:
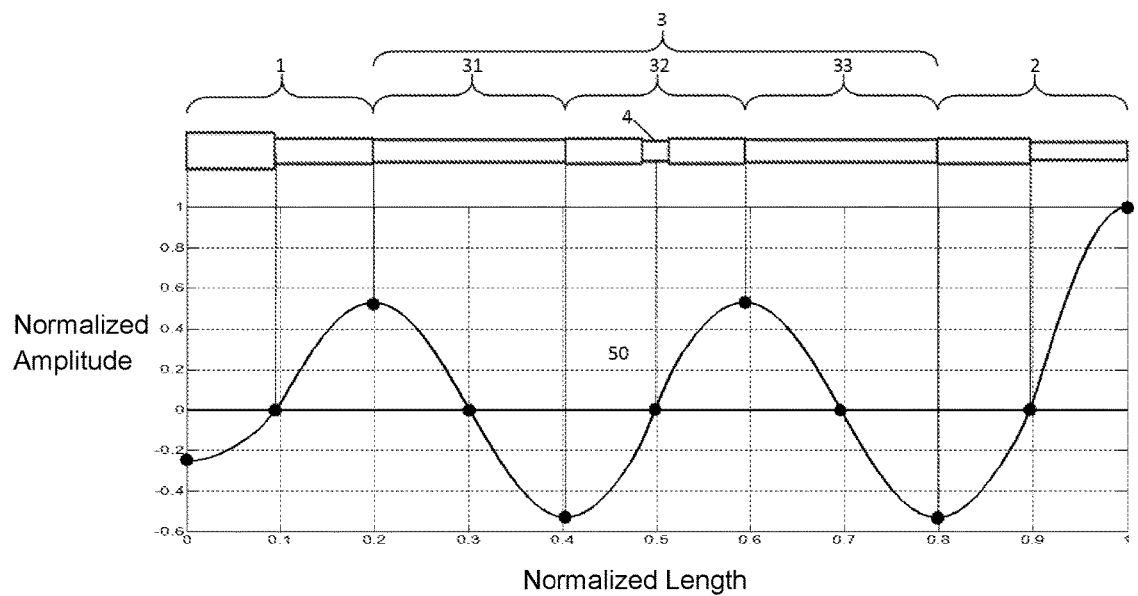
FIG. 3 shows a waveguide rod for an ultrasonic scalpel according to a third implementation manner of this application and a waveform generated along the waveguide rod.

FIG. 3 shows a waveguide rod for an ultrasonic scalpel according to a third implementation manner of this application and a waveform generated along the waveguide rod. The implementation manner comprises a proximal gain structure 1, a distal gain structure 2, an intermediate structure 3, and a frequency adjustment structure 4. The proximal gain structure is in a range of a first half wavelength of longitudinal vibration of the waveguide rod, and a most proximal gain step is near a first node of the longitudinal vibration. The distal gain structure is in a range of a last half wavelength of the longitudinal vibration of the waveguide rod, and a most distal gain step is near a last node of the longitudinal vibration. The proximal gain structure and the intermediate structure are connected in a position near a second antinode of the longitudinal vibration of the waveguide rod, and a gain of a proximal side gain step is greater than a unit gain. The distal gain structure and the intermediate structure are connected in a position near a second last antinode of the longitudinal vibration of the waveguide rod, and a gain of a distal side gain step is less than the unit gain. The intermediate structure in the implementation manner comprises three gain holding structures 31, 32, and 33, a gain of a first intermediate gain step is less than the unit gain, and a gain of a second intermediate gain step is greater than the unit gain. One frequency adjustment structure 4 exists on the gain holding structure 32 in the middle. A gain of a front frequency modulation gain step of the frequency adjustment structure is greater than the unit gain, and a gain of a rear frequency modulation gain step is less than the unit gain.

Figure 4:
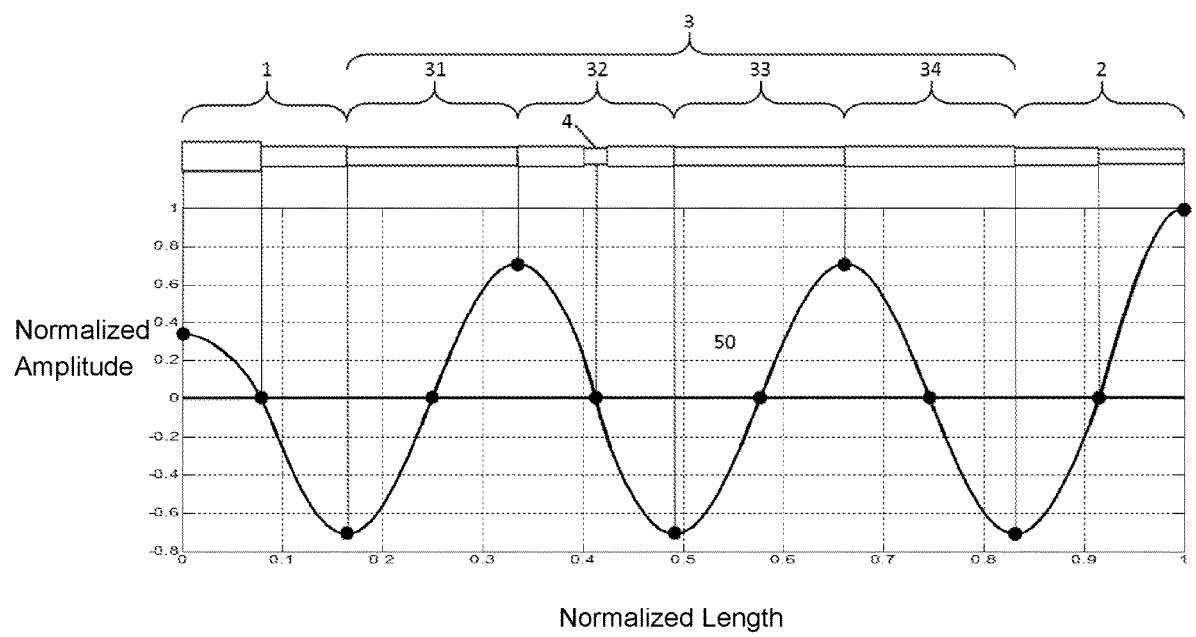
FIG. 4 shows a waveguide rod for an ultrasonic scalpel according to a fourth implementation manner of this application and a waveform generated along the waveguide rod.

FIG. 4 shows a waveguide rod for an ultrasonic scalpel according to a fourth implementation manner of this application and a waveform generated along the waveguide rod. The implementation manner comprises a proximal gain structure 1, a distal gain structure 2, an intermediate structure 3, and a frequency adjustment structure 4. The proximal gain structure is a range of a first half wavelength of longitudinal vibration of the waveguide rod, and a most proximal gain step is near a first node of the longitudinal vibration. The distal gain structure is in a range of a last half wavelength of the longitudinal vibration of the waveguide rod, and a most distal gain step is near a last node of the longitudinal vibration. The proximal gain structure and the intermediate structure are connected in a position near a second antinode of the longitudinal vibration of the waveguide rod, and a gain of a proximal side gain step is greater than a unit gain. The distal gain structure and the intermediate structure are connected in a position near a second last antinode of the longitudinal vibration of the waveguide rod, and a gain of a distal side gain step is greater than the unit gain. The intermediate structure in the implementation manner comprises four gain holding structures 31, 32, 33, and 34, and a gain sequence of the intermediate gain steps is formed by alternately arranging a gain less than the unit gain and a gain greater than the unit gain. One frequency adjustment structure 4 exists on the second gain holding structure 32. A gain of a front frequency modulation gain step of the frequency adjustment structure is greater than the unit gain, and a gain of a rear frequency modulation gain step is less than the unit gain.

Figure 5:
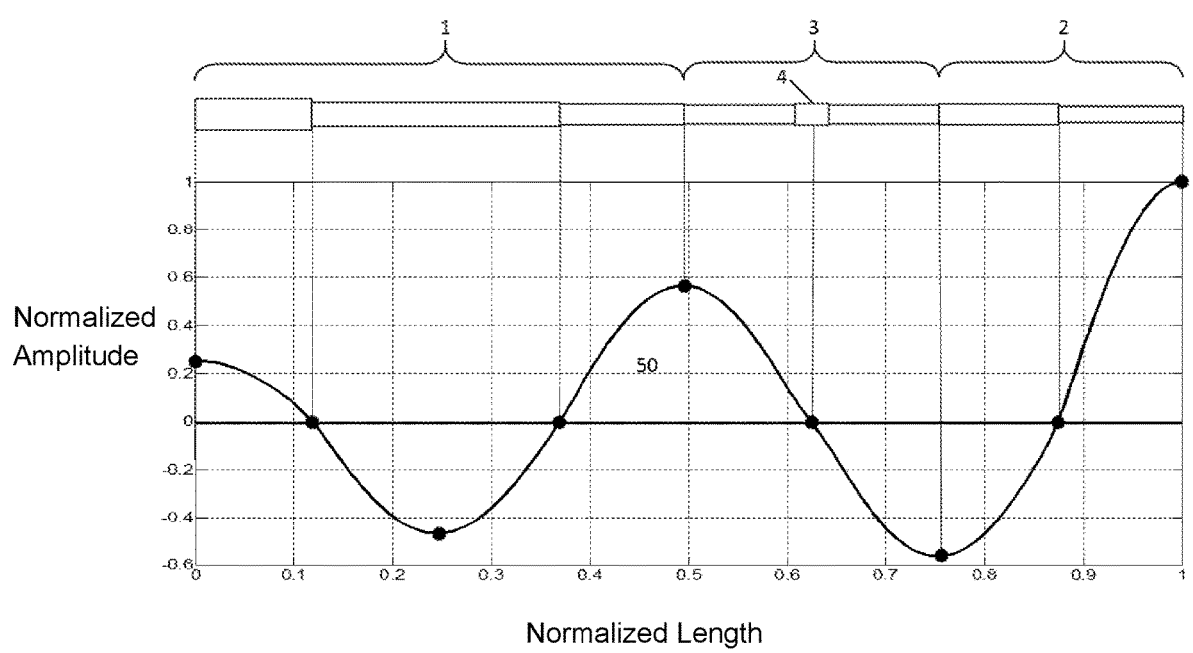
FIG. 5 shows a waveguide rod for an ultrasonic scalpel according to a fifth implementation manner of this application and a waveform generated along the waveguide rod.

FIG. 5 shows a waveguide rod for an ultrasonic scalpel according to a fifth implementation manner of this application and a waveform generated along the waveguide rod. The implementation manner comprises a proximal gain structure 1, a distal gain structure 2, an intermediate structure 3, and a frequency adjustment structure 4. The proximal gain structure is in a range of first two half wavelengths of longitudinal vibration of the waveguide rod, and a most proximal gain step is respectively near a first node and a second node of the longitudinal vibration. The distal gain structure is in a range of a last half wavelength of the longitudinal vibration of the waveguide rod, and a most distal gain step is near a last node of the longitudinal vibration. The proximal gain structure and the intermediate structure are connected in a position near a third antinode of the longitudinal vibration of the waveguide rod, and a gain of a proximal side gain step is greater than a unit gain. The distal gain structure and the intermediate structure are connected in a position near a second last antinode of the longitudinal vibration of the waveguide rod, and a gain of a distal side gain step is less than the unit gain. The intermediate structure in the implementation manner comprises only one gain holding structure. One frequency adjustment structure exists on the gain holding structure, a gain of a front frequency modulation gain step of the frequency adjustment structure is less than the unit gain, and a gain of a rear frequency modulation gain step is greater than the unit gain.

It should be noted that the gain steps in the examples of this application all have a stair form. However, the type of the gain steps is not limited in this application. Common gain step types such as a conical form, an exponential form, and a catenary form all fall within the protection scope of this application. In addition, the implementation solutions in FIG. 1 to FIG. 5 are only several relatively representative embodiments of this application. Persons skilled in the art may easily understand that the protection scope of this application is not merely limited to the ranges defined in the implementation manners, and combinations, deformations, and changes made to the implementation manners all fall within the protection scope of this application.

The invention claimed is:

1. A waveguide rod for an ultrasonic scalpel comprising:
a proximal gain structure;
a distal gain structure;
an intermediate structure; and
at least one frequency adjustment structure located on the intermediate structure, wherein
the proximal gain structure and the intermediate structure are connected at a position near an antinode of a longitudinal vibration of the waveguide rod through a proximal side gain step,
the distal gain structure and the intermediate structure are connected at a position near an antinode of the longitudinal vibration of the waveguide rod through a distal side gain step,
the intermediate structure comprises N gain holding structures, and when N is greater than one, the gain holding structures are connected two by two in a position near an antinode of the longitudinal vibration of the waveguide rod through an intermediate gain step,
the frequency adjustment structure is disposed on the gain holding structure, and a gain step is disposed on at least one of the proximal gain structure and the distal gain structure, in a position near a node of the longitudinal vibration of the waveguide rod.

2. The waveguide rod according to claim 1, wherein a gain of the proximal side gain step is one of greater than or less than a unit gain, and a distance between the proximal side gain step and the antinode is less than 5% of a half wavelength of the longitudinal vibration of the waveguide rod.

3. The waveguide rod according to claim 2, wherein the proximal side gain step is located in a position of the antinode of the longitudinal vibration of the waveguide rod.

4. The waveguide rod according to claim 1, wherein a gain of the distal side gain step is one of greater than or less than a unit gain, and a distance between the distal side gain step and the antinode is less than 5% of a half wavelength of the longitudinal vibration of the waveguide rod.

5. The waveguide rod according to claim 4, wherein the distal side gain step is located at a position of the antinode of the longitudinal vibration of the waveguide rod.

6. The waveguide rod according to claim 1, wherein the proximal gain structure is located in a range of a first half wavelength or a range of first two half wavelengths of the longitudinal vibration of the waveguide rod.

7. The waveguide rod according to claim 1, wherein the distal gain structure is located in a range of a last half wavelength or a range of last two half wavelengths of the longitudinal vibration of the waveguide rod.

8. The waveguide rod according to claim 1, wherein one or more proximal gain steps are disposed at a position near a node of the longitudinal vibration of the waveguide rod on the proximal gain structure,
a distance between each of the one or more proximal gain steps and the corresponding node is less than 5% of a half wavelength of the longitudinal vibration of the waveguide rod, and a gain of each proximal gain step is greater than a unit gain.

9. The waveguide rod according to claim 8, wherein each of the one or more proximal gain steps is located at a position corresponding to the corresponding node of the longitudinal vibration of the waveguide rod.

10. The waveguide rod according to claim 1, wherein one or more distal gain steps are disposed at a position near a node of the longitudinal vibration of the waveguide rod on the distal gain structure, a distance between each of the one or more distal gain steps and the corresponding node is less than 5% of a half wavelength of the longitudinal vibration of the waveguide rod, and a gain of each distal gain step is greater than a unit gain.

11. The waveguide rod according to claim 10, wherein each of the one or more distal gain steps is located at a position of the corresponding node of the longitudinal vibration of the waveguide rod.

12. The waveguide rod according to claim 1, wherein a distance between each intermediate gain step and the corresponding antinode of the longitudinal vibration of the waveguide rod is less than 5% of a half wavelength of the longitudinal vibration of the waveguide rod.

13. The waveguide rod according to claim 12, wherein each intermediate gain step is located at a position of the corresponding antinode of the longitudinal vibration of the waveguide rod.

14. The waveguide rod according to claim 1, wherein N is equal to 1.

15. The waveguide rod according to claim 1, wherein N is an odd number greater than 1.

16. The waveguide rod according to claim 15, wherein a gain sequence of the intermediate gain steps connecting the gain holding structures is: a gain of each of a first intermediate gain step to an ((N−1)/2)th intermediate gain step is greater than a unit gain, and a gain of each of an ((N−1)/2+1)th intermediate gain step to an (N−1)th intermediate gain step is less than the unit gain.

17. The waveguide rod according to claim 15, wherein a gain sequence of the intermediate gain steps connecting the gain holding structures is: a gain of each of a first intermediate gain step to an ((N−1)/2)th intermediate gain step is less than a unit gain, and a gain of each of an ((N−1)/2+1)th intermediate gain step to an (N−1)th intermediate gain step is greater than the unit gain.

18. The waveguide rod according to claim 15, wherein a gain sequence of the intermediate gain steps connecting the gain holding structures is formed by sequentially and alternately arranging a gain greater than a unit gain and a gain less than the unit gain.

19. The waveguide rod according to claim 15, wherein a gain sequence of the intermediate gain steps connecting the gain holding structures is formed by sequentially and alternately arranging a gain less than a unit gain and a gain greater than the unit gain.

20. The waveguide rod according to claim 1, wherein N is equal to 2.

21. The waveguide rod according to claim 20, wherein a gain of an intermediate gain step connecting two gain holding structures is greater than a unit gain.

22. The waveguide rod according to claim 20, wherein a gain of an intermediate gain step connecting two gain holding structures is less than a unit gain.

23. The waveguide rod according to claim 1, wherein N is an even number greater than 2.

24. The waveguide rod according to claim 23, wherein a gain sequence of the intermediate gain steps connecting the gain holding structures is formed by sequentially and alternately arranging a gain greater than a unit gain and a gain less than the unit gain.

25. The waveguide rod according to claim 23, wherein a gain sequence of the intermediate gain steps connecting the gain holding structures is formed by sequentially and alternately arranging a gain less than a unit gain and a gain greater than the unit gain.

26. The waveguide rod according to claim 1, wherein each frequency adjustment structure forms a front frequency modulation gain step and a rear frequency modulation gain step on a gain holding structure, only one node of the longitudinal vibration of the waveguide rod is disposed between the front frequency modulation gain step and the rear frequency modulation gain step, a distance between the front frequency modulation gain step and the rear frequency modulation gain step is less than a distance between two antinodes of the longitudinal vibration that are adjacent to a node, and one gain of the front frequency modulation gain step and the rear frequency modulation gain step is greater than a unit gain and the other gain is less than the unit gain.

27. The waveguide rod according to claim 26, wherein the gain of the front frequency modulation gain step is less than the unit gain, and the gain of the rear frequency modulation gain step is greater than the unit gain.

28. The waveguide rod according to claim 26, wherein the gain of the front frequency modulation gain step is greater than the unit gain, and the gain of the rear frequency modulation gain step is less than the unit gain.

* * * * *